United States Patent [19]

Schwartz

[11] Patent Number: 4,526,869
[45] Date of Patent: * Jul. 2, 1985

[54] METHOD FOR QUANTITATIVELY DETERMINING THE CONCENTRATION OF HEMOGLOBIN IN A BIOLOGICAL SAMPLE

[75] Inventor: Samuel Schwartz, St. Louis Park, Minn.

[73] Assignee: Regents of the University of Minnesota, Minneapolis, Minn.

[ * ] Notice: The portion of the term of this patent subsequent to Apr. 5, 2000 has been disclaimed.

[21] Appl. No.: 480,871

[22] Filed: Mar. 31, 1983

Related U.S. Application Data

[63] Continuation-in-part of Ser. No. 190,399, Sep. 24, 1980, Pat. No. 4,378,971.

[51] Int. Cl.³ .................. G01N 21/64; G01N 33/52; G01N 33/72
[52] U.S. Cl. .................. 436/66; 250/459.1; 356/40; 436/63; 436/172
[58] Field of Search .......... 250/459.1, 461.2; 356/40; 436/63, 66, 172

[56] References Cited

U.S. PATENT DOCUMENTS

| | | | |
|---|---|---|---|
| 2,290,436 | 7/1942 | Kamlet | 23/230 |
| 2,838,377 | 6/1958 | Fonner | 23/230 |
| 3,012,976 | 12/1961 | Adams, Jr. et al. | 252/408 |
| 3,092,463 | 6/1963 | Adams, Jr. et al. | 23/253 |
| 3,092,464 | 6/1963 | Adams, Jr. et al. | 23/253 |
| 3,252,762 | 5/1966 | Adams, Jr. et al. | 23/253 |
| 3,290,117 | 12/1966 | Adams, Jr. et al. | 23/253 |
| 3,663,175 | 5/1972 | Depositar et al. | 23/230 |
| 3,692,410 | 9/1972 | Jurány et al. | 356/40 |
| 3,718,431 | 2/1973 | Wild | 23/230 |
| 3,874,852 | 4/1975 | Hamill | 23/230 |
| 3,936,373 | 2/1976 | Studer | 209/17 |
| 3,964,865 | 6/1976 | Das | 23/230 |
| 4,005,984 | 2/1977 | Alsop | 23/230 |
| 4,017,261 | 4/1977 | Svoboda et al. | 23/253 |
| 4,035,150 | 7/1977 | Jaffe | 23/230 |
| 4,063,894 | 12/1977 | Ogawa et al. | 23/230 |
| 4,092,120 | 5/1978 | Suovaniemi et al. | 23/253 |
| 4,175,923 | 11/1979 | Friend | 23/230 |
| 4,199,550 | 4/1980 | Wielinger et al. | 422/48 |
| 4,219,336 | 8/1980 | Guthlein et al. | 23/230 |
| 4,378,971 | 4/1983 | Schwartz | 436/66 |

OTHER PUBLICATIONS

Morrison, Analytical Chemistry, vol. 37, pp. 1124–1126, (1965).
Grinstein, Journal of Biological Chemistry, vol. 167, pp. 515–519, (1947).
Research Disclosure, pp. 25–27, #17031, (Jun. 1978).
Sassa, Shigeru, "Sequential Induction of Heme Pathway Enzymes During Erythroid Differentiation of Mouse Friend Leukemia Virus-Infected Cells", *The Journal of Experimental Medicine*, vol. 143, (1976), pp. 305–315.
Wang, James C. C., and E. Russel Amiro, "A Fluorometric Method for the Microquantitative Determination of Haemoglobin and Myoglobin Concentrations in Fish Muscle", *Journal of the Science of Food and Agriculture* vol. 30, (1979), pp. 1089–1096.

Primary Examiner—Barry S. Richman
Assistant Examiner—Robert J. Hill, Jr.
Attorney, Agent, or Firm—Dorsey & Whitney

[57] ABSTRACT

A method for quantitatively determining the amount of hemoglobin in feces, urine or gastric juice comprising the steps of preparing a test sample of the feces, urine or gastric juice, converting the hemoglobin in the test sample to porphyrin with a converting reagent which is acidic and which has a reducing capacity sufficient to convert substantially all or a reproducible portion of the hemoglobin to porphyrin and determining the level of porphyrin in the test sample.

20 Claims, 2 Drawing Figures

METHOD FOR QUANTITATIVELY DETERMINING THE CONCENTRATION OF HEMOGLOBIN IN A BIOLOGICAL SAMPLE

BACKGROUND OF THE INVENTION

The present invention relates to a specific and quantitative test for hemoglobin in a biological sample such as feces, urine or gastric juice and is a continuation-in-part of my prior application Ser. No. 190,399 filed Sept. 24, 1980 which will issue on April 5, 1983 as U.S. Pat. No. 4,378,971. It is based on certain unique properties of heme (hemin), a natural pigment which combines with a protein (globin) to form hemoglobin. Heme itself is an iron complex of a class of red pigments called "porphyrin". When irradiated with appropriate wavelengths of light, porphyrins emit red fluorescence; heme does not. More particularly, then, the invention relates to a method and test for quantitatively determining the concentration of the heme pigment portion of hemoglobin in a biological material by removing iron from the non-fluorescing heme, thereby converting it to fluorescing porphyrin, and then assaying the fluorescence of the converted porphyrin. This test has particular applicability to a biological material such as feces, urine or gastric juice.

Various rapid screening tests for determining the presence of increased amounts of hemoglobin in biological materials such as feces are currently available. These tests are used throughout the medical profession as the primary screening test for intestinal tumors. It is estimated that in excess of ten million such tests are conducted each year in the United States for this purpose. Despite the fact that these tests do not yield quantitative data and that errors in test results are extremely costly, both personally and financially, and despite the fact that the tests currently available provide significantly high false positive and false negative results, their use is continued because there has been no alternative.

The screening tests which are currently available for hemoglobin in materials such as feces are indirect tests based on the peroxidase-like (pseudoperoxidase) activity of the hemoglobin. In the presence of hemoglobin, colorless leuco dyes, such as guaiac, become colored following addition of a suitable peroxide. Such tests, however, have several limitations. First, because of various factors including non-specificity and the fact that the reactivity is generally interfered with or affected by materials such as iron, ascorbic acid, or alterations in the hemoglobin molecule, significantly high false positive and false negative results are common. Secondly, interpretation of these tests is often confusing because test results are reported only as being "positive" or "negative". In addition to inherent differences in sensitivity of the different tests, test sensitivity varies greatly depending on the liquid content of the stool sample. The amount of feces included in test samples submitted may also vary by factors of ten or more. These factors, as well as the above-noted non-specificities and differences in personal interpretation of color development, all contribute to limiting the usefulness of these tests. Despite these limitations, occult blood assays based on leuco dyes are among the few remaining non-specific and non-quantitative tests in clinical and laboratory medicine.

From 1844 to 1960, several reports described the qualitative conversion of heme to porphyrins, with removal of iron effected by various acids and other special treatment. Almost all of these procedures were based on the use of blood or of the hemoglobin pigment, hemin, isolated from blood. These and similar procedures were also used for the purpose of preparing porphyrins from various other heme protein compounds such as cytochrome or myoglobin. However, these procedures did not disclose or suggest use in connection with a quantitative assay. Further, none referred to the use of feces, urine or gastric juice as sources of heme compounds or their quantitative assay in these procedures.

The application of this general approach to the quantitative estimation of hemoglobin or other heme compounds in tissue began with the report of G. R. Morrison entitled *Fluorimetric Microdetermination of Heme Protein,* (Anal. Chem., 37:1124–1126, 1965). He measured hemoglobin or other heme proteins in animal tissues by conversion of heme to porphyrin through the use of a saturated aqueous solution of oxalic acid heated to 100° C. or 120° C. He then assayed the fluorescence intensity of the porphyrin produced. This method, however, was effective for quantitatively determining hemoglobin only at very low levels of concentration. At concentrations which exceeded about 0.8 micrograms of hemoglobin per ml of oxalic acid solution, he reported that relatively little additional fluorescence was produced so that the method was totally ineffective at higher concentrations of hemoglobin. Since some fecal samples may have more than 100,000 times the maximum concentration found by Morrison to be assayable, feces having elevated levels of hemoglobin would have to be diluted several thousand-fold prior to heating in oxalic acid by Morrison's method. Such extreme dilution is not suitable for large-scale screening tests.

Another factor of great concern and importance is the presence of certain intestinal bacteria (presumed to be so-called "anaerobes") which convert hemoglobin heme to porphyrins in the gastrointestinal tract, mainly in the large bowel. The amount of such conversion varies among different individuals, but prior non-quantitative studies, as well as the studies conducted in accordance with the present invention, indicate that a major portion of hemoglobin present in the bowel may be converted to porphyrins in this way in some individuals. Because these porphyrins do not react with any of the leuco-dyes used in current tests of fecal blood, this bacterial effect may well be a major cause of false negative reactions found with prior leuco-dye tests.

Accordingly, there is a need in the art for an accurate and quantitative test for determining the amount of hemoglobin in biological materials such as feces, urine or gastric juice which eliminates or substantially reduces the incidence of false positive and false negative results, including those resulting from that fraction of hemoglobin converted to porphyrin by intestinal bacteria, and which is readily suitable for mass screening purposes.

SUMMARY OF THE INVENTION

The method of the present invention relates to a specific and quantitative test for hemoglobin in a biological material which eliminates false positive and false negative results and which has particular suitability for mass screening applications. The test to which the present invention relates has been shown to be (1) specific for heme compounds such as hemoglobin including both the total proto-heme content of the biological samples and that portion which is converted to porphyrins by intestinal bacteria, (2) free of interference from other materials in the sample, particularly those present in feces, urine or gastric juice, (3) extremely sensitive, (4) applicable for quantitative assay over a range of hemoglobin concentrations differing by a factor of more than 75,000, from concentrations of less than 0.02 micrograms per ml to more than 1,500 micrograms per ml of test solution, and (5) not significantly affected by compounds which may be present in feces, urine or gastric juice such as iron, ascorbic acid, hydrochloric acid, aspirin, cimetidine or alcohol which are known to affect some leuco-dye tests.

With the specific procedure of the present invention, non-fluorescing hemoglobin (heme) is converted quantitatively to fluorescing porphyrin at all concentrations of hemoglobin tested. This conversion takes place when heme compounds in the sample are combined with an effective quantity of a converting reaction mixture. In the preferred method, this converting reaction mixture has a relatively low pH and has a reducing capacity adequate to remove the iron molecule from the heme compounds. Free radical scavengers are also added in a preferred procedure to minimize side reactions, and heat is applied to the system to speed up the conversion reaction. Following this conversion, the heme-derived porphyrins are purified, the concentration of porphyrin is determined by a fluorescence assay, and such concentration is compared to a standard to determine the amount of hemoglobin in the sample.

It is believed that normal levels of hemoglobin in a fecal sample (including that portion which has been converted to porphyrin by bacteria) will usually range from about 0.2 to 1.0 milligrams (200 to 1000 micrograms) of hemoglobin per gram of feces in individuals on a diet which is free of "red" meat such as beef or pork. While on a diet of up to one-half pound of such meat daily, fecal hemoglobin levels may rise to 2 or 3 mg of hemoglobin per gram of feces. Elevated levels as high as 200 mg (200,000 micrograms) or more of hemoglobin per gram of feces have been found with severe bleeding. During preparation of the fecal sample, including addition of the converting reaction mixture, it is diluted approximately 250-fold so that the normal concentrations of hemoglobin in the diluted test sample range from about 1 to 10 micrograms of hemoglobin per ml (depending upon diet) and elevated levels can be as high as 1000 (or more) micrograms of hemoglobin per ml. In undiluted urine it is believed that normal levels of hemoglobin will be about 0.1 microgram of hemoglobin per ml which is the equivalent of about three red blood cells per microliter of urine. It is estimated that elevated levels could be as high as several thousand micrograms of hemoglobin per ml of sample in both urine and gastric juice. With a dilution of three-fold during preparation of the test sample for urine and a 20-fold dilution for gastric juice, the possible concentrations of hemoglobin range from less than 0.1 to several hundred micrograms of hemoglobin per ml of diluted sample.

To function satisfactorily, the converting reaction mixture should preferably be one that converts substantially all or a reproducible amount or portion of hemoglobin to porphyrin over the possible ranges of hemoglobin concentrations. When dealing with feces, urine or gastric juice, these concentrations can vary from very minimal levels of less than one microgram of hemoglobin per ml of solution to as high as 1000 (or more) micrograms of hemoglobin per ml of diluted solution, depending upon the degree of dilution. A satisfactory mixture would result in a substantially straight line or linear curve when concentration of hemoglobin is plotted against the fluorescence level of the converted porphyrin. The preferred mixture is a combination of a reducing acid such as oxalic acid and a reducing salt such as ferrous sulphate ($FeSO_4$). When this combination is used as the converting reaction mixture, a substantially linear relationship exists between hemoglobin concentration and fluorescence level of the converted porphyrin. However, mixtures other than oxalic acid and $FeSO_4$ will also convert hemoglobin to porphyrin at the possible ranges of hemoglobin concentrations. These other mixtures will function satisfactorily as the converting reaction mixture in the present invention provided substantially all or a reproducible amount or portion of the hemoglobin is converted to porphyrin. When this occurs, the amount of hemoglobin can be calculated by determining the level of converted porphyrins and comparing the same to a standard. With dilution factors similar to those mentioned above, the preferred converting reaction mixture should be one which converts substantially all or a reproducible amount or portion of hemoglobin to porphyrin at concentrations of hemoglobin at least about 40 micrograms/ml and preferably as high as several hundred micrograms per ml of diluted sample.

Feces, urine and gastric juice have fluorescence which is not related to porphyrins derived from hemoglobin. Under suitable conditions, the amount of such "non-specific" fluorescence (including that from porphyrins which are excreted normally) might be assayed separately and without purification in a second reagent which does not convert significant amounts of residual heme to porphyrins, but retains other fluorescing materials found with the conversion reagent. This condition is approximated with 1.5 molar citric acid, which generally converts less than 0.2 percent of hemoglobin heme to porphyrin under the recommended conditions. Under ideal circumstances, subtraction of the value obtained with the citric acid reagent from the total value obtained by the heme converting reagent yields a value which is due specifically to the porphyrin formed from hemoglobin as a result of the converting reaction mixture.

Although the use of a citric acid "blank" as described above has been found to be of value in certain applications, it is of limited value when applied to feces. A major reason is that about 20 to 70 percent of the heme which enters the gastrointestinal tract of adults is converted by certain intestinal bacteria to porphyrin. Thus, subtraction of values obtained in a citric acid "blank" will at best indicate only the concentration of residual heme in feces, not of total hemoglobin heme which entered the intestinal tract. In addition, non-specific compounds present often in feces, such as chlorophyll, do not fluoresce equally in the converting reagent and in the citric acid. Under these conditions, the citric acid cannot be a reliable "blank", even for residual heme. Finally, in some samples, heme-related fluorescence may be much less than one percent of the total initial fluorescence, so that calculation errors will be unacceptably high. The preferred method therefore separates the porphyrins derived from hemoglobin (both via intestinal bacteria and externally stimulated chemical conversion) from other interfering fluorescence prior to fluorimetric assay. This can be done with an appropriate purification or extraction procedure. With such a procedure, the citric acid reagent is included not as a "blank" but as a specific source of those porphyrins which are derived from heme by activity of intestinal bacteria.

Accordingly, an object of the present invention is to provide an improved test for specifically and quantitatively determining the amount of hemoglobin in a biological material.

A further object of the present invention is to provide an improved method for specifically and quantitatively determining the amount of hemoglobin in a test sample by converting the heme portion of the hemoglobin to porphyrin and assaying the fluorescence thereof.

A further object of the present invention is to provide an improved test for specifically and quantitatively determining the amount of hemoglobin in a biological test sample, which test has particular suitability for mass screening.

A further object of the present invention is to provide an improved method for specifically and quantitatively determining the amount of hemoglobin in a test sample of a biological material such as feces, urine or gastric juice over the range of possible hemoglobin concentrations in such samples.

A further object of the present invention is to provide an improved method for specifically and quantitatively determining the amount of hemoglobin in a feces, urine or gastric juice sample which utilizes a converting reaction mixture effective to convert substantially all or a reproducible amount or portion of hemoglobin to porphyrin over the entire range of possible hemoglobin concentrations.

A further object of the present invention is to provide a quantitative test for hemoglobin in feces, urine or gastric juice which accounts for conversion of heme by intestinal bacteria and which includes, in combination, a procedure for isolating heme-derived porphyrin.

Another object of the present invention is to provide an improved method for quantitatively determining the amount of hemoglobin in a test sample in which deleterious side reactions due to free radicals and other chemical substances is minimized.

These and other objects of the present invention will become apparent with reference to the drawings, the description of the preferred method and the appended claims.

DESCRIPTION OF THE PREFERRED METHOD

Figure 1:
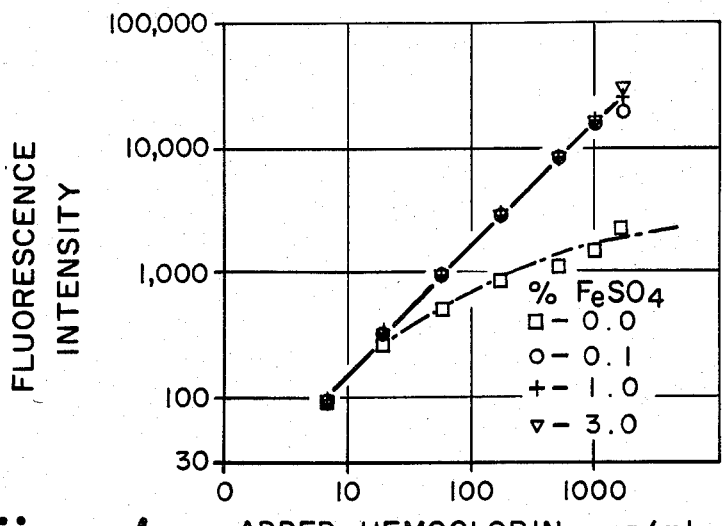
FIG. 1 is a graph plotting fluorescence intensity against hemoglobin concentration for converting reaction mixtures consisting of oxalic acid and varying amounts of ferrous sulfate.

The quantitative test utilizing the preferred procedure of the present invention includes four basic method steps. The first includes preparing a test sample of the biological material which is to be quantitatively tested for hemoglobin; the second includes quantitatively converting the non-fluorescing heme portion of the hemoglobin in the test sample to fluorescing porphyrin; the third includes purifying to eliminate non-specific fluorescence and interfering compounds; and the fourth includes assaying the fluorescence of the quantitatively retained porphyrin which is derived from hemoglobin, and comparing the same to a hemoglobin standard of known concentration. When applied to feces (but not to urine or gastric juice), the second step also includes a second reagent which does not convert heme to porphyrin but does retain porphyrins derived from heme by intestinal bacteria.

The preparation of the test sample includes the steps of collecting, mixing and determining the weight or volume of a test sample of the biological material of which the hemoglobin level is to be determined. While it is contemplated that the method of the present invention has applicability to many different biological materials, it has particular applicability to feces, urine and gastric juice samples. The description of the preferred method will be with reference to a fecal sample. A test quantity of the fecal sample is first collected and preferably kept frozen at $-15°$ C. until assayed.

The second method step of the present invention involves quantitatively converting the heme portion of hemoglobin in the test sample to porphyrin. This includes the substeps of mixing the test sample with an appropriate converting reaction mixture and heating the same. It also preferably includes the substeps of adding a free radical scavenger to reduce or eliminate deleterious side reactions.

The substep of mixing the test sample of feces with the converting reaction mixture includes mixing a suitable amount (i.e. 8.0 milligrams) of the test sample with a suitable volume (i.e. 2.0 ml) of a converting reaction mixture to convert the non-fluorescing heme portion of the hemoglobin to fluorescing porphyrin. While it is contemplated that many different converting reaction mixtures will be effective to quantitatively convert heme to porphyrin, such converting reaction mixtures must have sufficient reducing capacity to accomplish this conversion for the various anticipated concentrations of hemoglobin at the dilution level being utilized. Thus, the specific converting reaction mixtures which will be acceptable are dependent, in part, upon the extent to which the test sample has been diluted. If, as in the preferred procedure, 8.0 milligrams of a fecal sample are combined with 2.0 ml of the converting reaction mixture, the fecal sample, and thus the hemoglobin contained therein, will have been diluted approximately 250 fold. This dilution factor is determined by dividing the quantity (in milliliters) of converting reaction mixture (2.0 ml) by the quantity (in grams) of the fecal sample (0.008 grams). With a 250 fold dilution of the fecal sample, a normal hemoglobin level will be about 1 to 10 micrograms of hemoglobin per milliliter of diluted sample. To be acceptable as a converting reaction mixture, such mixture should preferably convert substantially all or a reproducible amount or portion of hemoglobin to porphyrin throughout a hemoglobin concentration range that would include the hemoglobin concentration of an individual having a fecal hemoglobin level about four times greater than normal. Thus, with a 250 fold dilution as described above, an acceptable converting reaction mixture would be one which has a reducing capacity sufficient to convert substantially all or a reproducible amount or portion of hemoglobin to porphyrin up to a hemoglobin concentration level of at least about 40 micrograms of hemoglobin per ml of diluted sample.

If the fecal sample is diluted to a greater extent, the hemoglobin concentration level over which the converting reaction mixture must be effective will be reduced. This will permit possible additional converting reaction mixtures to be utilized, (i.e.) those having insufficient reducing capacity to convert substantially all or a reproducible amount or portion of hemoglobin at a concentration of 40 micrograms/ml, but which do have sufficient reducing capacity at a lower hemoglobin level. For example, if the fecal sample is diluted 1000 fold, the converting reaction mixture would need to be effective only up to a hemoglobin concentration of about 10 micrograms/ml. Thus, the hemoglobin concentration level at which the converting reaction should be effective for a fecal sample is inversely proportional to the level of dilution. If one knows the level of dilution or the dilution factor, determined by dividing the quantity (in milliliters) of converting reaction mixture or other diluting solution by the quantity (in grams) of fecal sample, the hemoglobin concentration level (in micrograms per milliliter) at which the converting reaction mixture must be effective (about four times the hemoglobin level of a normal) can be determined by dividing 10,000 by the dilution factor. To be effective, a converting reaction mixture must have a reducing capacity sufficient to convert substantially all or a reproducible amount or portion of the hemoglobin to porphyrin over the concentration range in question.

One way of determining whether a particular converting reaction mixture is effective over a particular hemoglobin concentration range is to plot hemoglobin concentration against the fluorescence level of the converted porphyrin. If the resulting curve is substantially linear over the concentration range in question, the converting reaction mixture will be effective at these concentrations. The preferred converting reaction mixture which is comprised of oxalic acid and $FeSO_4$ shows a substantially linear relationship between hemoglobin concentration and fluorescence level of converted porphyrin up to at least a hemoglobin concentration of about 1000 micrograms/ml. Thus, substantially all of the hemoglobin is converted to porphyrin at these levels. This is illustrated best in FIG. 1 comprising a graph in which hemoglobin concentration is plotted against fluorescence level for several converting reaction mixtures of oxalic acid and various amounts of $FeSO_4$. The data used to generate this graph was obtained by heating samples of diluted blood to which oxalic acid and varying amounts (0.1% to 3%) of ferrous sulfate were added. As shown, oxalic acid in combination with varying amounts of ferrous sulfate is adequate to convert heme in diluted blood up to levels of at least 1,000 micrograms/ml. On the other hand, oxalic acid alone begins to show non-linearity at about the 10 to 15 microgram/ml level or lower. Thus, a fecal sample would have to be significantly diluted (on the order of at least about 1,000 fold) before oxalic acid alone would have reducing capacity sufficient for use as a converting reaction mixture.

A preferred converting reaction mixture contains 2.5 molar oxalic acid and 0.09 molar $FeSO_4$. Also included in this mixture is 0.05 molar uric acid and 0.1 molar mannitol which function as free radical scavengers. The inclusion of these additional components will be discussed in further detail below. During the conversion reaction, iron is removed from the non-fluorescing heme molecule, resulting in the iron-free fluorescing protoporphyrin and other porphyrins which fluoresce red on exposure to near ultraviolet light. Maximum intensity of fluorescence in this acid solution is produced by illumination (excitation) with approximate wavelengths of 400–406 nanometers (nm). Because the individual porphyrins present have slightly different excitation and emission maxima, wide ($\pm 20$ nm) slits are used. The mixture of porphyrins produced also fluoresces, though less intensely, when exposed to green or yellow light at the approximate wavelengths of 550–555 or 595–600 nm. In addition to protoporphyrin, significant amounts of what appear to be hematoporphyrin and isomers of monovinyl-monohydroxyethyl intermediates are also formed from heme in the reaction with oxalic acid:ferrous sulfate. Several additional porphyrins with similar fluorescence properties are formed from heme by intestinal bacteria.

Figure 2:
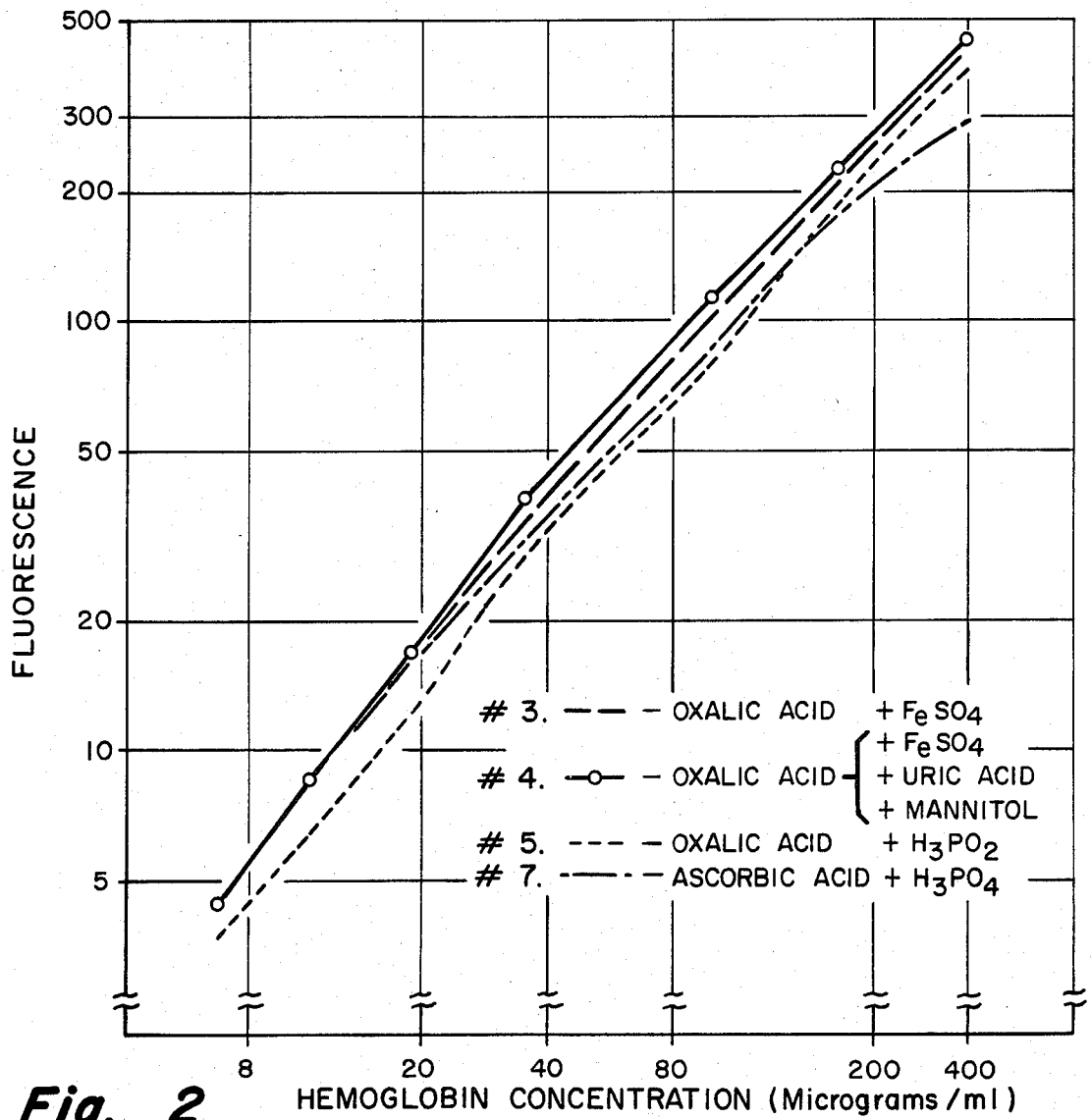
FIG. 2 is a graph plotting fluorescence intensity against hemoglobin concentration for various converting reaction mixtures.

Although the oxalic acid:ferrous sulfate system is preferred, other systems will also work. In this respect, conversion tests were conducted on several other possible converting reaction mixtures. In each of these conversion tests, known amounts of hemoglobin (blood) were added to aliquots of a normal fecal material containing 0.71 milligrams of hemoglobin per gram of feces to produce fecal samples with seven different known concentrations of hemoglobin. Each of ten different possible converting reaction mixtures was then used in performing the quantitative test of the present invention on duplicates of each of the above-mentioned seven fecal samples. In each test, 8.0 mg of the fecal sample were combined with 2.0 ml of the converting reaction mixture. The samples were then heated for twenty minutes in a boiling water bath (100° C.) and the three step extraction procedure described below was performed on aliquots of the samples. A fluorescence analysis was conducted on each sample. The results which reflect average values for the duplicate analyses are set forth in Table 1. Results from four of these mixtures are also shown in FIG. 2 in which concentrations of added hemoglobin are plotted against fluorescence level.

TABLE 1

| Fluorescence (in thousands) for Various Hemoglobin Concentrations (in micrograms/ml)* | | | | | | | | |
|---|---|---|---|---|---|---|---|---|
| Test No. | Converting Reagent** | 6.9 | 11.0 | 19.2 | 35.6 | 101.0 | 199.0 | 398.0 |
| 1 | Oxalic acid (only) | 4.60 | 8.83 | 14.4 | 26.5 | 56.7 | 71.0 | 144.0 |
| 2 | Oxalic acid:$SnCl_2$ | 4.82 | 8.48 | 17.8 | 37.8 | 97.6 | 146.0 | 213.0 |
| 3 | Oxalic acid:$FeSO_4$ | 4.36 | 8.23 | 17.5 | 35.3 | 108.0 | 221.0 | 420.0 |
| 4 | Oxalic acid:$FeSO_4$:U.A.:M | 4.25 | 8.66 | 16.6 | 39.0 | 118.0 | 231.0 | 455.0 |
| 5 | Oxalic acid:$H_3PO_2$ | 3.77 | 6.45 | 12.0 | 29.0 | 84.6 | 203.0 | 390.0 |
| 6 | Oxalic acid:$H_3PO_3$ | 2.83 | 4.38 | 6.0 | 8.4 | 17.4 | 17.0 | 41.0 |
| 7 | Ascorbic acid:$H_3PO_4$ | 4.97 | 8.79 | 16.2 | 32.2 | 91.9 | 191.0 | 306.0 |
| 8 | $H_3PO_2$:$FeSO_4$ | 2.10 | 2.51 | 4.8 | 21.4 | 32.3 | 53.0 | 116.0 |
| 9 | $H_3PO_3$:$FeSO_4$ | 1.69 | 2.30 | 3.3 | 5.8 | 10.9 | 25.0 | 34.0 |

TABLE 1-continued

| Fluorescence (in thousands) for Various Hemoglobin Concentrations (in micrograms/ml)* | | | | | | | |
|---|---|---|---|---|---|---|---|
| Test No. | Converting Reagent** | 6.9 | 11.0 | 19.2 | 35.6 | 101.0 | 199.0 | 398.0 |
| 10 | Citric Acid | 1.38 | 1.43 | 1.4 | 1.4 | 2.0 | 3.6 | 7.0 |

*In each case, duplicate samples were prepared by adding 8.0 mg of feces to 2.0 ml of converting reagent. Samples were heated for 20 minutes in a boiling water bath (100° C.). Aliquots were purified by an extraction procedure. The data reflects average values of fluorescence for duplicate analyses.
**Concentration of Reagents:
Oxalic acid - 2.5 M
$FeSO_4$ - 0.09 M
$SnCl_2$ - 0.01 M
U.A. (Uric acid) - 0.05 M
M (Mannitol) - 0.10 M
$H_3PO_2$ (Hydrophosphorous acid) - 1 M
$H_3PO_3$ (Orthophosphorous acid) - 1 M
$H_3PO_4$ (Phosphoric acid) - 2 M
Ascorbic acid - 2 M
Citric acid - 1.5 M As shown by the results set forth in Table 1 and FIG. 2, certain of the converting reaction mixtures tested showed a greater conversion of heme to porphyrin than others, particularly at higher hemoglobin concentrations. For example, the converting reaction mixtures of oxalic acid:$FeSO_4$ (#3) and oxalic acid:$FeSO_4$:uric acid:mannitol (#4) showed the highest level of conversion throughout the entire range of hemoglobin concentrations considered in this test system. Thus, these converting reaction mixtures are preferred. Other systems display relatively good conversion at lower hemoglobin concentrations, but poorer conversion at higher concentration levels. For example, in addition to the two systems mentioned above, oxalic acid alone (#1), oxalic acid:$SnCl_2$ (#2), oxalic acid:$H_3PO_2$ (#5) and ascorbic acid:$H_3PO_4$ (#7) show relatively good conversion at lower concentrations. However, conversion with the oxalic acid alone (#1) begins to decrease at hemoglobin concentrations above about 15 micrograms per ml of reagent while conversion with oxalic acid:$SnCl_2$ (#2) begins to decrease at about 75-100 micrograms/ml and ascorbic acid:$H_3PO_4$ (#7) begins to decrease about 20-30 micrograms/ml. The oxalic acid:$H_3PO_2$ (#5) system shows generally decreased fluorescence levels over the entire hemoglobin concentration range, but still a generally linear relationship. Thus, these four systems (#1, #2, #5 and #7) will work as converting reaction mixtures although it is clear that #1, #2 and #7 will be effective (substantially linear) for a hemoglobin concentration of up to about 15, 75-100 and 20-30 micrograms/ml, respectively. The other systems in Table 1 (with the exception of citric acid), show lower fluorescence yields at all hemoglobin concentrations, but nevertheless still show some relationship between hemoglobin concentration and fluorescence level. It is believed that the sample would have to be significantly diluted before any of these would be effective. The citric acid system shows minimal conversion and is therefore unacceptable for use as a converting reaction mixture in the present procedure.

Systems other than the preferred system of oxalic acid:ferrous sulfate described above would be acceptable in varying degrees as a converting reaction mixture if they convert substantially all or a reproducible amount or portion of heme to porphyrin at the relevant concentrations. Some, however, such as reagents #1, #2, #5 and #7, will function better with additional dilution of the sample, thus reducing the relevant concentration levels. In general, the greater the degree of conversion by a particular reagent, the more acceptable that reagent will be in the present procedure. Safety will also normally play a significant role in determining which reagent to utilize. For example, although reagents such as $H_3PO_2$, $H_2SO_4$ and HCl will function acceptable as part of a converting reaction mixture, they are more hazardous to work with than the preferred oxalic acid:$FeSO_4$ system. Any reducing reagent, however, which is capable of converting substantially all or a reproducible amount or portion of heme to porphyrin under the conditions employed (i.e.), amounts and duration of heating, dilution of the sample, the degree to which deleterious side reactions are controlled or eliminated by use of a free radical scavenger as described below, etc. will be acceptable.

The extent and rapidity, and thus the effectiveness, of the converting reagent in removing iron from the heme molecule to liberate fluorescing porphyrin is dependent primarily upon a combination of two chemical factors: (1) the reducing capacity of the reagent system and (2) the acidity or pH of the reagent system.

While oxalic acid alone has sufficient reducing capacity and a sufficiently low pH to be effective as a converting reagent at relatively low hemoglobin concentrations, other reducing acids such as ascorbic acid, require addition of a stronger acid to achieve a desirably low pH. Acids such as phosphoric, formic, sulfuric, hydrochloric and tartaric are sufficiently low in pH, but they must be supplemented by the addition of a reducing salt and/or other reducing compound. To function adequately as a converting reaction mixture in accordance with the present invention, the pH of such mixture, at 25° C., should be less than 2 and preferably less than about 1.3.

As described above, ferrous sulfate ($FeSO_4$) is combined with oxalic acid or various other reducing acids for the purpose of increasing the reducing capacity of the system. It has been found that various other reducing salts and other compounds will also work. For example, various ferrous, manganous, stannous, cobaltous and nickel salts such as ferrous oxalate, manganous sulfate ($MnSO_4$), stannous chloride ($SnCl_2$), nickel chloride ($NiCl_2$), cobaltous chloride ($CoCl_2$) and dithiothreitol will function to improve the reducing capacity of a converting reaction system. Hypophosphorous acid ($H_3PO_2$) has also been shown to be effective for the purpose of increasing the reducing capacity of the system.

Other factors can also affect the conversion of heme to porphyrin and the types of porphyrin formed. For example, although the reaction converting heme to porphyrin will proceed to some extent at room temperature, the speed and degree of the reaction will be improved by the addition of heat. Various types of heat sources have been utilized including autoclaves (110° C.

for 90 minutes), boiling or hot water baths (80° to 100° C. for 20 minutes or more), and microwave ovens for a few minutes or less. All have been found acceptable for use in conjunction with the method of the present invention although heating at about 100° C. has the advantage of simplicity and improved fluorescence yield in the preferred system. The temperature and the duration of heating affects not only the speed of conversion, but also the composition of the resulting porphyrins. If the temperature is too high, some of the porphyrins can be destroyed as a result of deleterious side reactions. Although this can be minimized to some extent by the use of free radical "scavengers" such as uric acid and mannitol, the temperature normally should not exceed 120° C. Preferably, the temperature should be between about 90° C. and 110° C.

The duration of heating necessary will depend upon the converting reagent temperature and type of heat source. Conversion is also more rapid in diluted blood than in feces, and appears to be in part at least related to the complete mixing of the test sample. While a variety of different temperatures and dwell times will be acceptable, the temperature and dwell time should be effective to convert substantially all, or a reproducible portion, of the heme to porphyrin. In a preferred method, the system is heated for twenty minutes at a temperature of about 100° C.

The amount of final porphyrin recovered may also be affected significantly by the formation of reactive products, including so-called "free radicals" which may alter or destroy heme, and to a lesser degree, the porphyrins formed. These effects are influenced by the particular chemical components of the system or by constituents of the sample tested. The production of such free radicals is well known in systems which contain ferrous iron ("Fenton Reaction") as is the case in the preferred converting reagent of oxalic acid and $FeSO_4$. By adding a component to the converting reaction mixture which readily reacts with these various free radicals and functions to remove them from the system, the destruction or alteration of heme or of converted porphyrins can be minimized and the accuracy of the test improved. Several so-called "scavengers" of free radicals have been tested to determine which ones protect heme and porphyrins most from the deleterious side reactions which may accompany heating or treatment with the converting components of the converting reagent. Of those tested, uric acid and mannitol provided the best results. In a preferred method, 0.05 molar uric acid and 0.1 molar mannitol are used.

In general, any system which is sufficiently acidic (less than a pH of about 2) and which has sufficient reducing capacity to remove the iron from the heme molecules in the test sample is capable of functioning as the converting reagent in accordance with the present invention. Although some systems are better than others because of their greater efficiency and reproducibility in converting heme to fluorescing porphyrin, it should be noted that any reagent which converts a major (preferably greater than about 50%) and reproducible portion of heme to porphyrin can be used to quantitatively determine the level of hemoglobin in the test sample pursuant to the procedure of the present invention.

Following mixing of the test sample with the converting reagent and heating, an extraction or purification procedure is preferably performed on the resulting mixture to isolate and purify the porphyrins derived from hemoglobin. In the above-mentioned resulting mixture, several contaminants exist which will affect the ability to accurately determine the level of porphyrin derived from hemoglobin when the level of porphyrin is determined by a fluorescence assay as employed in the preferred procedure, or by an absorbance assay. It is desirable to eliminate these interfering components which can include elements such as naturally occurring porphyrins, chlorophyll and various other materials having a fluorescence wavelength which coincides with the wavelength of converted porphyrin.

In the preferred procedure, the method of isolating and separating the porphyrins derived solely from the conversion of the heme portion of hemoglobin involves three general extraction or purification steps which are more specifically described in my copending application Ser. No. 418,282 filed Sept. 13, 1982. The first step involves shaking the mixture with a solvent. This is preferably an organic solvent such as ethyl acetate containing a small amount of glacial acetic acid which is capable of extracting those porphyrins whose ultimate determination is desired, namely, the porphyrins derived from hemoglobin. In a preferred automated procedure, the ethyl acetate:acetic acid reagent is replaced by a combination of isobutyl alcohol, diisopropylbenzene and acetic acid in a 6:4:1 ratio, respectively.

The second step of the purification procedure involves adding an aqueous solvent to extract impurities including naturally occurring porphyrins such as coproporphyrin. Specifically, this step includes the addition of n-butyl alcohol to the ethyl acetate extract and shaking it with an aqueous alkaline solution. In the preferred automated procedure, the supernatent from step one is shaken directly with an aqueous alkaline solution.

A third extraction step is then performed to extract the porphyrins derived from hemoglobin, leaving behind red-fluorescing chlorophyll and other "fat soluble" materials. This third step involves extracting the porphyrin from the ehtyl acetate:butyl alcohol (or isobutyl alcohol:diisopropylbenzene) phase by a 9:1 mixture of two molar phosphoric acid and glacial acetic acid.

The final step of the preferred procedure of the present invention is determining the level of converted porphyrin in the test sample. This preferably utilizes a fluorescence assay in which a determination of the fluorescence level of the converted porphyrin is made by known procedures and then compared to a standard prepared in a similar fashion with known concentrations of (converted) hemoglobin or cyanmethemoglobin. When a converting reagent is used which reproducibility converts substantially all of the heme to porphyrin, the concentration of precursor heme, and thus hemoglobin, in the test sample can be directly calculated.

Although the description of the preferred method has been quite specific, it is contemplated that various changes could be made without deviating from the spirit thereof. Accordingly, it is intended that the scope of the present invention be dictated by the appended claims rather than by the description of the preferred embodiment.

I claim:

1. A method of quantitatively determining the amount of hemoglobin in feces, urine or gastric juices comprising the steps of:

preparing a test sample of feces, urine or gastric juices;

converting hemoglobin in said test sample to porphyrin by combining said test sample with an acidic converting reagent, said converting reagent being selected from the group of converting reagents having a reducing capacity sufficient to convert the hemoglobin in said test sample to porphyrin so that said conversion is substantially linear for concentrations of hemoglobin as high as 40 micrograms of hemoglobin per milliliter; and determining the level of porphyrin in said test sample.

2. The method of claim 1 wherein said steps of preparing a test sample and converting the hemoglobin in said test sample to porphyrin includes diluting said test sample to form a diluted solution.

3. The method of claim 1 including substantially isolating the porphyrin from contaminants.

4. The method of claim 1 including heating said combined test sample and converting reagent to a temperature of between about 80° C. and 120° C.

5. The method of claim 1 wherein the level of porphyrin is determined by a fluorescence assay.

6. The method of claim 1 wherein said converting reagent has a reducing capacity sufficient to convert substantially all of the hemoglobin.

7. The method of claim 1 wherein said converting reagent is selected to have a reducing capacity sufficient to convert the hemoglobin in said sample to porphyrin so that said conversion is substantially linear for concentrations of hemoglobin as high as 100 micrograms of hemoglobin per milliliter.

8. The method of claim 1 wherein said converting reagent has a pH of no more than 2.

9. The method of claim 8 wherein said converting reagent includes the combination of:
an acid component comprised of one or more of the compounds selected from the group consisting of oxalic acid, ascorbic acid, formic acid, sulfuric acid, hydrochloric acid, phosphoric acid, hypophosphorus acid and orthophosphorus acid; and
a reducing component comprised of one or more of the compounds selected from the group consisting of ferrous salts, manganous salts, stannous salts, cobaltous salts, nickel salts and dithiothreitol.

10. The method of claim 1 including the adding a second reagent to said combined test sample and converting reagent for reacting with free radicals formed during the conversion of hemoglobin to porphyrin.

11. The method of claim 10 wherein said second reagent includes uric acid and mannitol.

12. A method of quantitatively determining the amount of hemoglobin in feces comprising the steps of:
preparing a test sample of feces;
converting hemoglobin in said test sample to porphyrin by combining said test sample with an acidic converting reagent, said converting reagent being selected from the group of converting reagents having a reducing capacity sufficient to convert the hemoglobin in said test sample to porphyrin so that said conversion is substantially linear for concentrations of hemoglobin as high as 40 micrograms of hemoglobin per milliliter; and
determining the level of porphyrin in said test sample.

13. The method of claim 12 wherein said converting reagent includes a combination of:
an acid component comprised of one or more of the compounds selected from the group consisting of oxalic acid, ascorbic acid, formic acid, sulfuric acid, hydrochloric acid, phosphoric acid, hypophosphorous acid and orthophosphorous acid; and
a reducing component comprised of one or more of the compounds selected from the group consisting of ferrous salts, manganous salts, stannous salts, cobaltous salts, nickel salts and dithiothreitol.

14. The method of claim 12 wherein said steps of preparing a test sample and converting the hemoglobin in said test sample to porphyrin includes diluting said test sample to form a diluted solution.

15. The method of claim 12 including heating said combined test sample and converting reagent to a temperature of between about 80° C. and 120° C.

16. The method of claim 12 wherein the level of porphyrin is determined by a fluorescence assay.

17. The method of claim 12 wherein said converting reagent has a reducing capacity sufficient to convert substantially all of the hemoglobin.

18. The method of claim 12 wherein said converting reagent is selected to have a reducing capacity sufficient to convert the hemoglobin in said test sample to porphyrin so that said conversion is substantially linear for concentrations of hemoglobin as high as 100 micrograms of hemoglobin per milliliter.

19. The method of claim 12 wherein said converting reagent has a pH of no more than 2.

20. The method of claim 19 wherein said converting reagent includes a combination of:
an acid component comprised of one or more of the compounds selected from the group consisting of oxalic acid, ascorbic acid, formic acid, sulfuric acid, hydrochloric acid, phosphoric acid, hypophosphorous acid and orthophosphorous acid; and
a reducing component comprised of one or more of the compounds selected from the group consisting of ferrous salts, manganous salts, stannous salts, cobaltous salts, nickel salts and dithiothreitol acid and orthophosphorous acid.

* * * * *

UNITED STATES PATENT AND TRADEMARK OFFICE
CERTIFICATE OF CORRECTION

PATENT NO. : 4,526,869

DATED : July 2, 1985

INVENTOR(S) : Samuel Schwartz

It is certified that error appears in the above-indentified patent and that said Letters Patent is hereby corrected as shown below:

In col. 1, line 5, before the "BACKGROUND OF THE INVENTION" heading, please add the following:

"This invention was made with government support under R01-AM 12466 and GM 14086 awarded by the National Institutes of Health. The government has certain rights in the invention."

Signed and Sealed this

First Day of November, 1994

Attest:

BRUCE LEHMAN

*Attesting Officer*         *Commissioner of Patents and Trademarks*